(12) United States Patent
Li et al.

(10) Patent No.: US 11,103,603 B2
(45) Date of Patent: Aug. 31, 2021

(54) $^{18}$F-LABELED COMPOUNDS FOR PET IMAGING AND USES THEREOF (71) Applicant: The University of North Carolina at Chapel Hill, Chapel Hill, NC (US)

(72) Inventors: Zibo Li, Chapel Hill, NC (US); Zhanhong Wu, Chapel Hill, NC (US); Ben Giglio, Henrico, VA (US); Stergios Moschos, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/343,267

(22) PCT Filed: Oct. 20, 2017

(86) PCT No.: PCT/US2017/057595
§ 371 (c)(1),
(2) Date: Apr. 18, 2019

(87) PCT Pub. No.: WO2018/128664
PCT Pub. Date: Jul. 12, 2018

(65) Prior Publication Data
US 2019/0247527 A1     Aug. 15, 2019

Related U.S. Application Data

(60) Provisional application No. 62/410,681, filed on Oct. 20, 2016.

(51) Int. Cl.
*A61K 51/00* (2006.01)
*A61M 36/14* (2006.01)
*A61K 51/04* (2006.01)
*C07B 59/00* (2006.01)
*A61P 35/00* (2006.01)

(52) U.S. Cl.
CPC .......... *A61K 51/0406* (2013.01); *A61P 35/00* (2018.01); *C07B 59/002* (2013.01); *A61K 2123/00* (2013.01); *C07B 2200/05* (2013.01)

(58) Field of Classification Search
CPC . A61K 51/0406; A61K 2123/00; A61P 35/00; C07B 59/002; C07B 2200/05
USPC ...................................................... 424/1.89
See application file for complete search history.

(56) References Cited

U.S. PATENT DOCUMENTS 4,695,588 A * 9/1987 Kollonitsch .......... C07D 233/64
514/419
2005/0069495 A1* 3/2005 Baranowska-Kortylewicz ..........
A61K 51/0491
424/1.73

FOREIGN PATENT DOCUMENTS

TW      20517922       5/2015
WO      2016/040458    3/2016

OTHER PUBLICATIONS

Henrottin et al. Nucl. Med. Biol. 2016, 379-389.*
Lambrecht et al. J. Nucl. Med. 1974, 863-867.*
Weiss et al. Bioorg. Med. Chem. 2015, 5856-5869.*
Ferried Handbook Radiopharm.: Radiochem. Appl. 2003, 229-282.*
Batista et al. Mol. Imaging Biol. 2009, 11,460-466.*
Eakins J. Labelled Cmpd Radiopharm. 1979, 148-149.*
Meng et al. Cancer Treat. Rev. 2015, 868-876.*
Eriksson et al. Nucl. Med. Biol. 2012, 567-575.*
Li et al. Appl. Radiat. Isot. 2010, 303-308.*
Corr et al. Tetrahedron 2016, 7306-7310.*
International Preliminary Report on Patentability corresponding to PCT/US2017/057595, dated May 2, 2019.
Chotellis et al. "Synthesis, Radiolabeling, and Biological Evaluation of 5-Hydroxy-2-[18F]fluoroalkyl-tryptophan Analogues as Potential PET Radio tracers for Tumor Imaging", Journal of medicinal chemistry pp. 1-27 (2016).
Chirakal et al. "Synthesis of f-18 labelled fluoro-melatonins and 5-hydroxyfluoro-tryptophans", J. of labeled compounds and radiopharmaceuticals XXV(1):63-71 (1988).
Chugani et al. "Alpha[C-11 ]methyl-L-tryptophan PET maps brain serotonin synthesis and kynurenine pathway metabolism", Journal of Cerebral Blood Flow Metabolism 20(1):2-9 (2000).
Hou et al. "Inhibition of Indoleamine 2,3-dioxygenase in dendritic cells by stereoisomers of 1-methyl-tryptophan correlated with anti-tumor responses", Cancer Res 67(2):792-801 (2007).
International Search Report and Written Opinion corresponding to International Application No. PCT/US2017/057595 dated Nov. 8, 2016.
Xie et al. "Development of 1-N-11 C-Methyl-1- and -d-Tryptophan for Pharmacokinetic imaging of the immune checkpoint inhibitor 1-Methyl-Tryptophan", Scientific Reports 5:16417 (2015) (9 pages).
Muller et al. "Differential targeting of tryptophan catabolism in tumors and in tumor-draining lymph modes by stereoisomers of the IDO inhibitor 1-methyltryptophan", International Congress Series 1304(1): 250-261 (2007) (Abstract Only).

* cited by examiner

Primary Examiner — Michael G. Hartley
Assistant Examiner — Sean R Donohue
(74) Attorney, Agent, or Firm — Myers Bigel, P.A.

(57) ABSTRACT

The present invention relates to $^{18}$F-labeled compounds suitable for positron emission tomography (PET) imaging. The invention further relates to the use of these compounds for carrying out PET scans, imaging the indoleamine 2,3-dioxygenase, pathway, predicting the responsiveness of a subject with a solid tumor to therapies including immunotherapy such as PD-1/PD-L1 inhibition, and determining whether a solid tumor in a subject contains tumor-infiltrating immune cells.

8 Claims, 8 Drawing Sheets

[18]F-LABELED COMPOUNDS FOR PET IMAGING AND USES THEREOF

STATEMENT OF PRIORITY

This application is a 35 U.S.C. 371 national phase application of PCT Application PCT/US2017/057595 filed Oct. 20, 2017, which claims the benefit of U.S. Provisional Application Ser. No. 62/410,681, filed Oct. 20, 2016, the entire contents of each of which are incorporated by reference herein in its entirety.

FIELD OF THE INVENTION

The present invention relates to $^{18}$F-labeled compounds suitable for positron emission tomography (PET) imaging. The invention further relates to the use of these compounds for carrying out PET scans, imaging the indoleamine 2,3-dioxygenase pathway, predicting the responsiveness of a subject with a solid tumor to therapies, including immunotherapy such as PD-1/PD-L1 inhibition, and determining whether a solid tumor in a subject contains tumor-infiltrating immune cells.

BACKGROUND OF THE INVENTION

Monoclonal antibodies targeting co-inhibitory immune checkpoint proteins, such as CTLA4 and PD-1/PD-L1, constitute a growing class of anticancer agents that were recently FDA approved for treatment of metastatic melanoma (MM) and non-small cell lung cancer, and are currently in advanced stages of clinical development in a half dozen other cancers (e.g., urothelial cancer, renal cell carcinoma, Merkel cell carcinoma) (Buque et al. *Oncoimmunology* 4: e1008814 (2015); Antonia et al., *Clin. Cancer Res.* 20:6258 (2014)). In contrast to the tremendous progress in developing companion diagnostics that would reliably predict response to small molecule inhibitors (usually identification of a hot spot mutation by sequencing of DNA isolated from patient's tumor tissue) (Dietel et al. *Cancer Gene Ther.* 22:417 (2015)), less progress has been achieved for development of biomarkers that predict response to this expensive class of monoclonal antibodies. The situation will only become more challenging as more targeted therapies against various other co-stimulatory and co-inhibitory immune checkpoint proteins are currently being tested alone or in combination (Antonia et al., *Clin. Cancer Res.* 20:6258 (2014)). Studies in melanoma and in urothelial cancers have shown that a pre-existing immune response (which includes tumor-infiltrating immune cells that fail to eradicate cancers due to various immunosuppressive mechanisms within the tumor microenvironment, along with expression of PD-L1 in the proximity of tumor-infiltrating immune cells) is fundamental for response to PD-1/PD-L1 pathway inhibitors (Tumeh et al., *Nature* 515:568-571 (2014); Powles et al., abstr 5011, *ASCO Annual Meeting* (Chicago, Ill., 2014)). Currently, development of a companion diagnostic that predicts response to PD-1/PD-L1 pathway inhibitors is limited only to the immunohistochemical detection of PD-L1 in tumor tissue. Apart from focusing solely on only one of the two fundamental aspects of response to PD-1/PD-L1 pathway inhibitors, development of PD-L1 assays has significant technical, methodological, and biological limitations. In contrast to oncogenic driver mutations that are consistently present, PD-L1 expression is heterogeneous and shows extreme variability in relation to the stage of disease (primary versus metastatic), prior systemic treatment, organ type of involvement by the tumor, amount (in $mm^2$ surface area) of tumor tissue available, antibody type for assay development, expression cutoffs, etc. (Dietel et al. *Cancer Gene Ther.* 22:417 (2015); Tumeh et al., *Nature* 515:568-571 (2014); Powles et al., abstr 5011, *ASCO Annual Meeting* (Chicago, Ill., 2014); Madore et al., *Pigment Cell Melanoma Research* 28:245 (2014)) Clearly, the development of novel molecular imaging probes that can predict response to such immunotherapies is appealing, because it can capture the status (and by extension the heterogeneity) of melanoma immediately prior to treatment. Unfortunately, conventional fludeoxyglucose $^{18}$F-FDG-PET, or even the more recently applied fluorothymidine $^{18}$F-FLT-PET imaging, cannot differentiate metabolic activity derived from melanoma versus immune system activation. Development of PET tracers that specifically identify immune system functioning within the tumor has become clinically and therapeutically relevant/important.

Indoleamine 2,3-dioxygenase (IDO1) has a special role in the biology of melanoma and other cancers. It can be an inducible enzyme within melanoma and other tumor-infiltrating immune regulatory cell subsets, which catalyzes the rate-limiting first step in tryptophan catabolism. It therefore depletes an essential amino acid in favor of toxic catabolites. The end result is suppression of antitumor response, predominantly via reduction of cytotoxic T-cell activity and proliferation of T regulatory (Treg) cells. In fact, upregulation of IDO1 is significantly correlated with the number of $CD8^+$ T cells and PD-L1 expression in a small number of melanoma tumor biopsies, suggesting a coordinated upregulation of at least three immunosuppressive mechanisms in the microenvironment of "inflamed" melanomas (Spranger et al., *Science Transl. Med.* 5: 200ra116 (2013)).

The present invention overcomes shortcomings in the art by providing PET probes suitable for use as an IDO pathway probe and methods of using the probes to predict tumor response and treat tumors.

SUMMARY OF THE INVENTION

As high IDO expression in tumor tissues coexists with other immunoregulatory mechanisms in melanomas that exhibit underlying immune response (the so called 'inflamed' melanomas), it is expected that high IDO activity would only 'mark' 'immunogenic' cancers, i.e., those who will most likely respond to PD-1/PD-L1 pathway inhibitors. If IDOL is coexpressed in cancers other than melanoma then PET imaging of the IDO pathway may be a more global non-invasive method of identifying cancers with pre-existing immune response (i.e., inflamed).

In line with this, there are PET probes that image the IDO pathway currently in clinical use for various intracranial and extracranial conditions. The most broadly studied in human disease is a $^{11}$C-based tryptophan analogue, $^{11}$C-alpha-methyl-L-tryptophan ($^{11}$C-AMT). Immunohistochemical studies in human tissues that were collected following $^{11}$C-AMT imaging showed significant correlation between standard uptake value of $^{11}$C-AMT and immunohistochemical expression of components of the tryptophan uptake and metabolism of the kynurenine pathway in breast cancer (Juhasz et al., *Nuclear Med. Biol.* 39:926 (2012)), primary brain tumors (Batista et al., *Mol. Iimaging Biol.* 11:460-466 (2009)), and childhood seizures (Chugani et al., *Soc. Neurosci. Ann. Mtg.* 24:1757 (1998)). Unfortunately, clinical studies so far have been limited to single institutions with capability to produce their own $^{11}$C-AMT due to its extremely short half-life (20 min). There is an urgent need to develop $^{18}$F-based tryptophan analogs that share some of the properties of AMT (i.e., inability to participate in protein synthesis) with similar or even more specificity for the kynurenine (IDO related) as opposed to the indoleamine or the deamination/decarboxylation pathway (Ball et al., *Frontiers Immunol.* 5:485 (2014)).

Development of monoclonal antibody therapies against immune checkpoint proteins is a rapidly growing area of preclinical and clinical research with indication across multiple solid tumors. However, the cost of such therapies, most of which are to be administered for a lifetime or until tumor progression or intolerable toxicity, is substantial (Saltz, Perspectives on Value. in *ASCO* (ed. Meeting, A. A.) (Chicago, Ill., 2015)). Obviously, expenses double if administered in combination (Larkin et al. *New Engl. J. Med.* 373:23 (2015)). On average, the number of cancer patients to treat in order to achieve antitumor responses is approximately 3 for every 10 (Sui et al., *Oncotarget* 6: 19393 (2015)). The medical oncology field was 'caught unprepared' in terms of having reliable predictive biomarkers of response for immuno-oncology drugs. Companion diagnostics for targeted therapies are more reliable because the target of interest is usually a driver oncogenic mutation which by definition is present throughout cancer development and progression; this implies that tumor tissues collected from any stage or organ site of involvement will almost always contain the target whose expression may remain unaltered despite different treatments. In contrast, antitumor immune response is contextual, and heterogeneous in both space (i.e., organs involved) and time as tumors evolve through various anticancer treatments, both local and systemic. PET imaging, therefore, is ideal to quantify and control for this heterogeneity. PET tracers that image the IDO pathway, and in particular $^{11}$C-AMT, have been used for more than 15 years in non-invasive imaging of various benign and malignant conditions. However, the short half-life of $^{11}$C tracers has limited widespread use.

Although IDO has been best investigated in melanoma and is overexpressed in melanomas with high numbers of tumor-infiltrating lymphocytes, interrogation of the RNAseq data as part of the Cancer Genome Atlas Project suggests that IDO1 overexpression may correlate with underlying immune response in other cancer types as well. Table 1 shows RNAseq data corresponding to 5 different genes from each of 5 different cancers other than melanoma, as part of the Cancer Genome Atlas Project. These TCGA data are presented via the cbioportal for Cancer Genomics (cbioportal.org). Apart from the IDO1 gene, the two genes that comprise CD8, the specific surface molecule of effector T cells, and FoxP3, the transcription factor that is specifically expressed in naturally occurring T regulatory cells, are shown. Log odds ratio quantifies how strongly the presence or absence of alteration of gene A (IDO1) is associated with the presence or absence of alterations in gene B (PD-L1, CD8A, CD8B, FoxP3), along with the corresponding level of statistical significance. Similar to cutaneous melanoma, IDO mRNA expression in most cancers significantly correlates with expression of other genes that are uniquely expressed by tumor-infiltrating immune cells. This implies that IDO1 coexists with other aspects of antitumor immune response.

TABLE 1

| Gene A | Gene B | Colorectal (n = 382) | | Breast (n = 1,100) | | Lung Adeno (n = 517) | | Lung Squamous (n = 501) | | Prostate (n = 498) | | Head & Neck Squamous (n = 522) | |
|---|---|---|---|---|---|---|---|---|---|---|---|---|---|
| | | p-value | Log odds ratio | p-value | Log odds ratio | p-value | Log odds ratio | p-value | Log odds ratio | p-value | Log odds ratio | p-value | Log odds ratio |
| IDO1 | PD-L1 | <0.001 | >3.0 | <0.001 | >3.0 | 0.050 | 1.2 | 0.176 | 0.617 | <0.001 | 2.4 | 0.002 | 1.3 |
| IDO1 | CD8A | 0.019 | 2.8 | <0.001 | 2.1 | <0.001 | 2.4 | <0.001 | 2.3 | <0.001 | >3.0 | <0.001 | 2.7 |
| IDO1 | CD8B | 0.149 | 2.2 | <0.001 | 2.1 | <0.001 | 1.9 | 0.379 | 0.9 | <0.001 | 2.1 | <0.001 | 2.1 |
| IDO1 | FOXP3 | 0.247 | 1.5 | <0.001 | 2.8 | 0.028 | 1.0 | 0.380 | 0.4 | <0.001 | 2.9 | 0.134 | 0.7 |

Given the fact that multiple mechanisms of immunosuppression may coexist in the microenvironment of melanomas with 'immune-high' signature, including overexpression of IDO (Prendergast et al., *Cancer Immunol. Immunother.: CII* 63:721 (2014)), it is expected that in vivo imaging of the IDO pathway may assist in selecting out patients who have a preexisting immune response, and therefore respond to PD-1 pathway inhibitors. $^{11}$C-AMT, an analogue of tryptophan, is an inhibitor of IDO, but not a substrate of protein synthesis. $^{11}$C-AMT has been previously used as a PET tracer in tuberous sclerosis complex-related epilepsy and brain tumors in human studies. In fact, high $^{11}$C-AMT uptake by glioblastoma tumors was an adverse prognostic factor.

Figure 1:
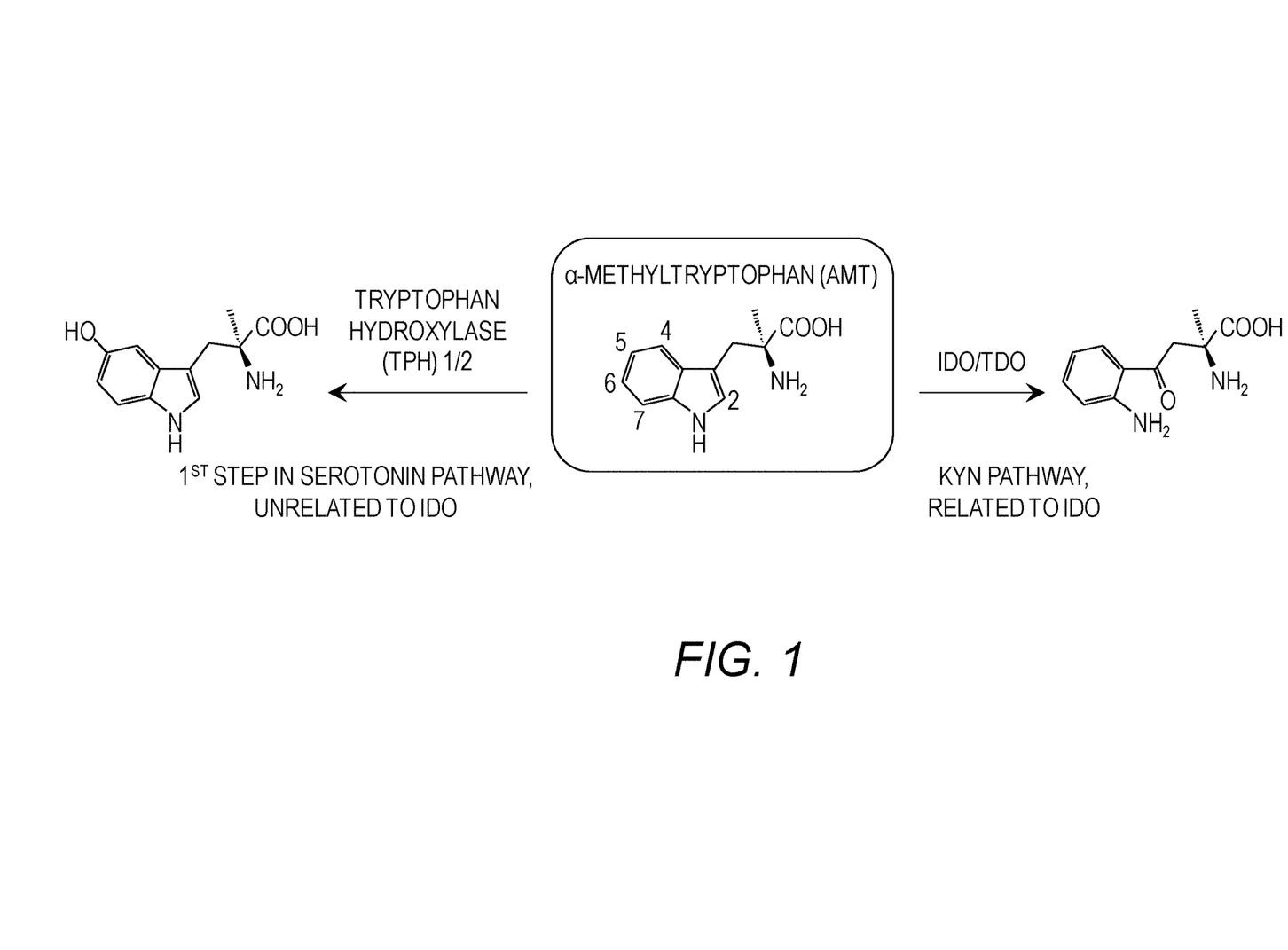
FIG. 1 shows that $^{11}$C-AMT is involved in both serotonin and kynurenine pathways.

Despite its great potential, $^{11}$C-AMT PET has two critical limitations. First, $^{11}$C-AMT could participate in both serotonin and kynurenine (Kyn) pathways (FIG. 1). The Kyn pathway involves IDO1, IDO2, or TDO2; and serotonin involves tryptophan hydroxylase (Tph). A PET probe that is more specific to Kyn pathway is highly preferred (closely related to IDO). Second, the short half-life (20 min) of $^{11}$C-AMT inherently limits its mass production and commercial distribution for broader application, including multicenter clinical trials. Moreover, the synthetic route for $^{11}$C-AMT is rather complicated involving computer controlled automated modules, air/moisture sensitive materials during radiolabeling, and harsh conditions (−50° C. without air and moisture for labeling reaction, followed by heating at 135° C. in TFA (highly corrosive), and 160° C. in KOH). All the above factors limit the wide application of $^{11}$C-AMT. With its half-life of 109.8 min, low β$^{+}$-energy (0.64 MeV), and ease of production, $^{18}$F has been the ideal radionuclide for routine PET imaging, as evidenced by the widespread clinical use of FDG in hematology/oncology. Due to its low positron energy it has a short positron linear range in tissue, leading to particularly high resolution in PET imaging. Furthermore, compared to other PET radionuclides (such as $^{11}$C), its half-life is long enough to allow syntheses, transportation, and imaging procedures to be extended over hours, while limiting the amount of radiation doses for the patient. Clearly, a $^{18}$F labeled IDO probe is more preferred since it will allow the agent to be more broadly used. The present invention is based on the development of $^{18}$F-labeled PET tracers that are more specific to IDO, which can be used in non-invasive predictive methods to select patients responsive (or resistant) to anti-PD-1 mAb-based therapies.

Accordingly, one aspect of the invention relates to a $^{18}$F-labeled compound suitable for use as an IDO pathway probe, e.g., tryptophan or an analog thereof.

A further aspect of the invention relates to a PET probe comprising the compound of the invention.

An additional aspect of the invention relates to a composition comprising the compound or probe of the invention and a pharmaceutically acceptable carrier.

Another aspect of the invention relates to the compounds $^{18}$F-labeled serotonin and $^{18}$F-labeled melatonin.

A further aspect of the invention relates to a method of carrying out a PET scan on a subject, comprising administering to the subject the compound, probe, or composition of the invention.

An additional aspect of the invention relates to a method of imaging the IDO pathway in a subject, comprising administering to the subject the compound, probe, or composition of the invention.

Another aspect of the invention relates to a method of predicting the responsiveness of a subject with a solid tumor to a PD-1/PD-L1 inhibitor, comprising carrying out a PET scan on the subject using the compound, probe, or composition of the invention.

A further aspect of the invention relates to a method of treating a solid tumor in a subject, comprising predicting the responsiveness of a subject with a solid tumor to a PD-1/PD-L1 inhibitor by carrying out a PET scan on the subject using the compound, probe, or composition of the invention, and treating the solid tumor based on the results of the PET scan.

An additional aspect of the invention relates to a method of determining whether a solid tumor in a subject contains tumor-infiltrating immune cells, comprising carrying out a PET scan on the subject using the compound, probe, or composition of the invention.

Another aspect of the invention relates to a method of treating a disease or disorder, e.g., cancer, e.g., a solid tumor, in a subject in need thereof, comprising administering a therapeutically effective amount of a therapeutic compound or composition of the invention.

The present invention is explained in greater detail in the drawings herein and the specification set forth below.

DETAILED DESCRIPTION OF THE INVENTION

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Unless the context indicates otherwise, it is specifically intended that the various features of the invention described herein can be used in any combination.

Moreover, the present invention also contemplates that in some embodiments of the invention, any feature or combination of features set forth herein can be excluded or omitted.

To illustrate, if the specification states that a complex comprises components A, B and C, it is specifically intended that any of A, B or C, or a combination thereof, can be omitted and disclaimed singularly or in any combination.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

The term "consists essentially of" (and grammatical variants), as applied to the compositions of this invention, means the composition can contain additional components as long as the additional components do not materially alter the composition. The term "materially altered," as applied to a composition, refers to an increase or decrease in the therapeutic effectiveness of the composition of at least about 20% or more as compared to the effectiveness of a composition consisting of the recited components.

"Treat" or "treating" or "treatment" refers to any type of action that imparts a modulating effect, which, for example, can be a beneficial effect, to a subject afflicted with a disorder, disease or illness, including improvement in the condition of the subject (e.g., in one or more symptoms), delay or reduction in the progression of the condition, and/or change in clinical parameters, disease or illness, etc., as would be well known in the art.

The term "therapeutically effective amount" or "effective amount," as used herein, refers to that amount of a composition, compound, or agent of this invention that imparts a modulating effect, which, for example, can be a beneficial effect, to a subject afflicted with a disorder, disease or illness, including improvement in the condition of the subject (e.g., in one or more symptoms), delay or reduction in the progression of the condition, prevention or delay of the onset of the disorder, and/or change in clinical parameters, disease or illness, etc., as would be well known in the art. For example, a therapeutically effective amount or effective amount can refer to the amount of a composition, compound, or agent that improves a condition in a subject by at least 5%, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

A "treatment effective" amount as used herein is an amount that is sufficient to provide some improvement or benefit to the subject. Alternatively stated, a "treatment effective" amount is an amount that will provide some alleviation, mitigation, decrease or stabilization in at least one clinical symptom in the subject. Those skilled in the art will appreciate that the therapeutic effects need not be complete or curative, as long as some benefit is provided to the subject.

"Pharmaceutically acceptable," as used herein, means a material that is not biologically or otherwise undesirable, i.e., the material can be administered to an individual along with the compositions of this invention, without causing substantial deleterious biological effects or interacting in a deleterious manner with any of the other components of the composition in which it is contained. The material would naturally be selected to minimize any degradation of the active ingredient and to minimize any adverse side effects in the subject, as would be well known to one of skill in the art (see, e.g., *Remington's Pharmaceutical Science*; 21$^{St}$ ed. 2005). Exemplary pharmaceutically acceptable carriers for the compositions of this invention include, but are not limited to, sterile pyrogen-free water and sterile pyrogen-free physiological saline solution.

Figure 2:
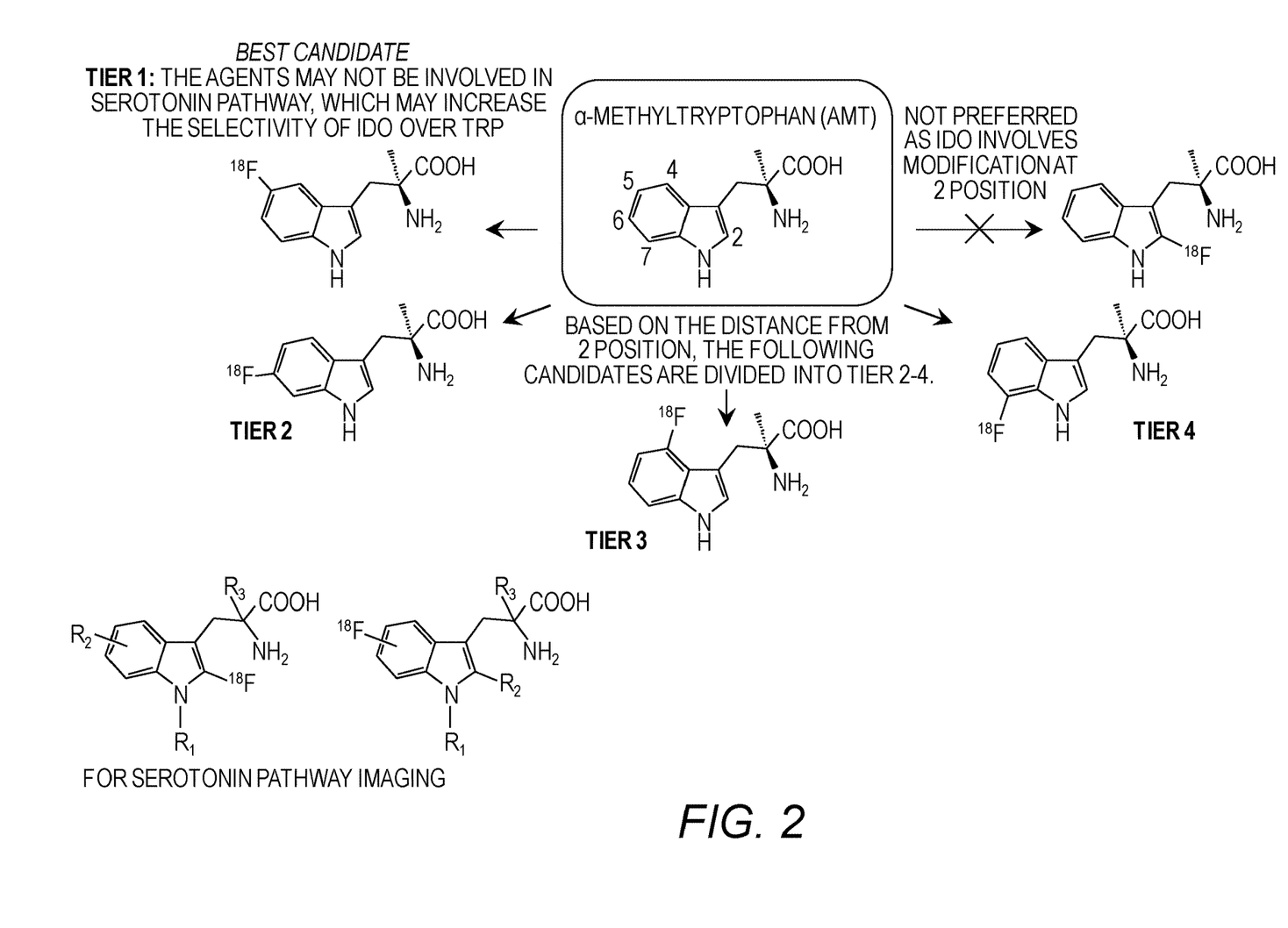
FIG. 2 shows PET agents for IDO imaging and serotonin pathway imaging.

Various $^{18}$F-labeled tryptophan analogs have been reported. Most such analogues are L-tryptophan analogs, which participate in protein synthesis and multiple metabolic pathways (Kramer et al., *J Nuclear Med.* 53:434 (2012); Chiotellis et al., *Eur. J. Med. Chem.* 70:768 (2013); Chiotellis et al., *Mol. Pharm.* 11:3839 (2014); Hamid et al., *New Engl. J. Med.* 369:134 (2013); Shih et al., *Biomed. Res. Int* 0.2014: 492545 (2014)). AMT does not participate in protein synthesis due to the presence of an α-methyl group [—C(CH$_3$)NH$_2$COOH instead of CHNH$_2$COOH]; of note the methyl group does not interfere with catabolism since both kynurenine and serotonin pathways target the aromatic part of this amino acid for degradation. Although AMT could participate in both serotonin and kynurenine (Kyn) pathways, analysis on child brain lesions using $^{11}$C-AMT PET demonstrated increased production of quinolinic acid (Kyn pathway, involves IDO1, IDO2 or TDO2) instead of serotonin (involves tryptophan hydroxylase (Tph)) (Chugani et al., *Soc. Neurosci. Ann. Mtg.* 24:1757 (1998)). Nonetheless, it is ideal to have a PET agent that is preferentially metabolized by one pathway to simplify the modeling and reduce unnecessary complexity. The present goal was to develop an analog that mimics AMT instead of a simple tryptophan derivative, because tryptophan derivatives participate in multiple metabolic pathways, and therefore the imaging results would be complicated to interpret, including low contrast due to high background activity. The products of the present invention are based on the AMT core structure, which can be modified by introducing $^{18}$F at the 2, 4, 5, 6, or 7-position of AMT (FIG. 2). Given that the Kyn pathway involves the formation of N-formyl kynurenine (breaks at carbon 2), modification at the 2-position may be avoided to maintain IDO reactivity. As the serotonin pathway will form 5-hydroxytryptophan (un-wanted), some embodiments of the invention comprise modifications at position-5, aiming to improve IDO specificity over Tph because replacing the C—H bond with a C—F bond may block the metabolic pathway at the 5 position (similar to $^{18}$F-FDG vs. glucose). Representative $^{18}$F-AMT agents are shown in FIG. 2.

Figure 3:
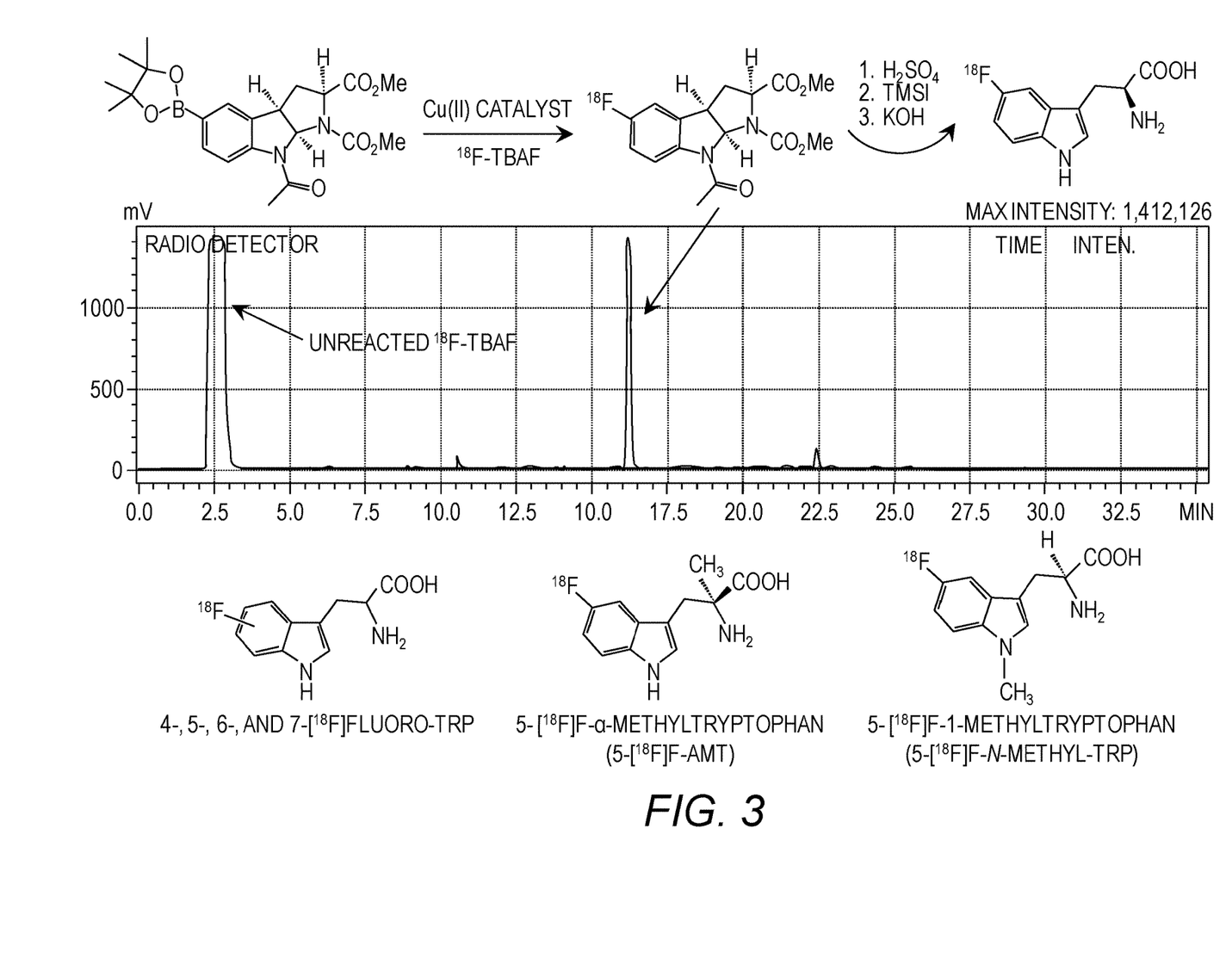
FIG. 3 shows a method to introduce $^{18}$F on the tryptophan aromatic ring and potential IDO PET agents.

To synthesize Tier 1 compounds as shown in FIG. 2, electrophilic fluorination could have been the easiest approach. Unfortunately, electrophilic $^{18}$F-fluorination suffers from several well-recognized drawbacks from a radiochemistry point of view. Carrier added methods are generally used for the production of [$^{18}$F]F$_2$ gas, which would lead to labeled products with low specific activity (SA). In addition, cyclotron produced [$^{18}$F]F$_2$ is a reagent that requires special equipment for its handling, which can react unselectively and lead to a mixture of products. This complication could lower the radiochemical yield (RCY) and make the final product difficult to purify. In contrast, $^{18}$F—F$^-$ could be produced in large amounts with high SA. It would be ideal if compounds could be made from $^{18}$F—F$^-$, which is difficult to achieve on an electron-rich aromatic ring. We achieved success by radiolabeling the fully protected Trp analog (FIG. 3).

Synthesis of the compounds of the invention may be carried out by methods known in the art and as described herein. In some embodiment, the synthetic route comprises dissolving the boronic ester of the compounds to be labeled in the presence of a copper catalyst. $^{18}$F is added and the reaction heated. An acid (e.g., H$_2$SO$_4$) is added to quench the reaction. HPLC may be used to purify the desired product. An exemplary synthetic scheme is shown below.

Figure 4:
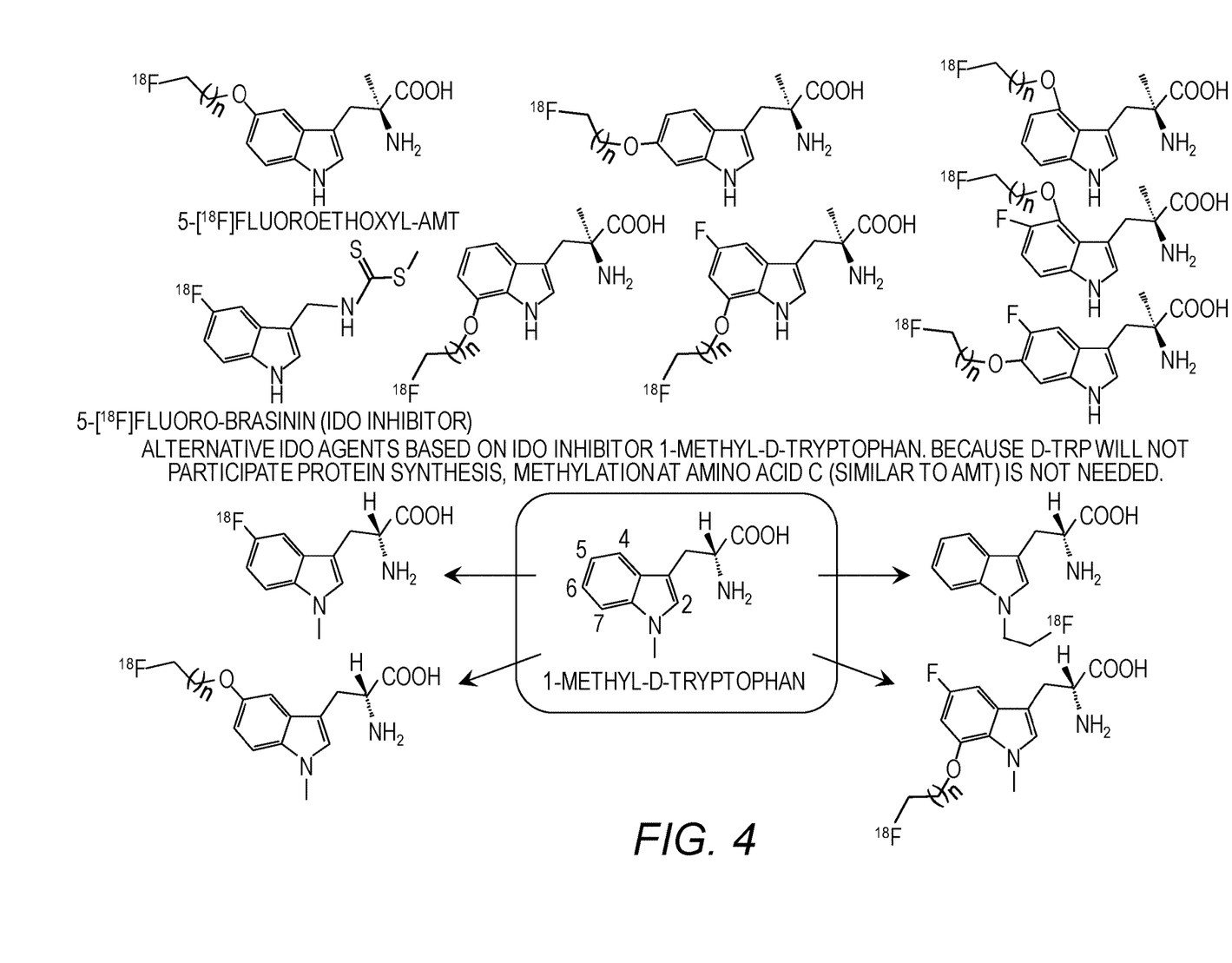
FIG. 4 shows compounds of the invention.
Figure 5:
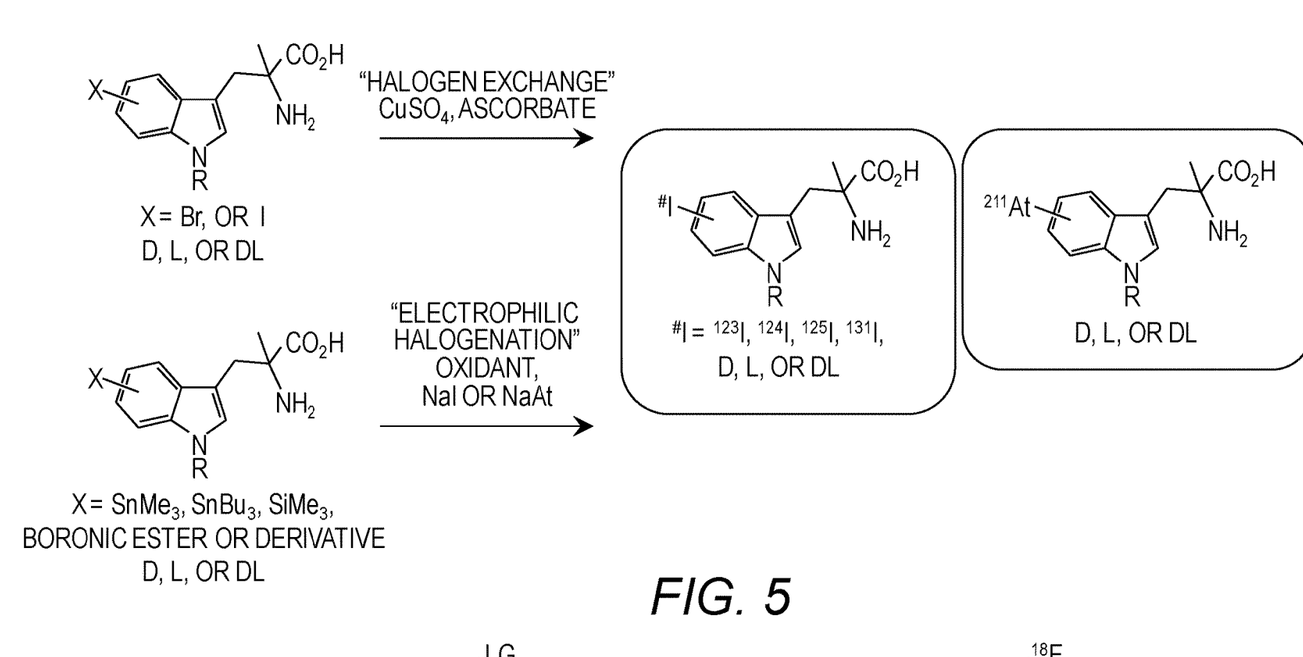
FIG. 5 shows halo-AMT derivatives for imaging or therapy.
Figure 6:
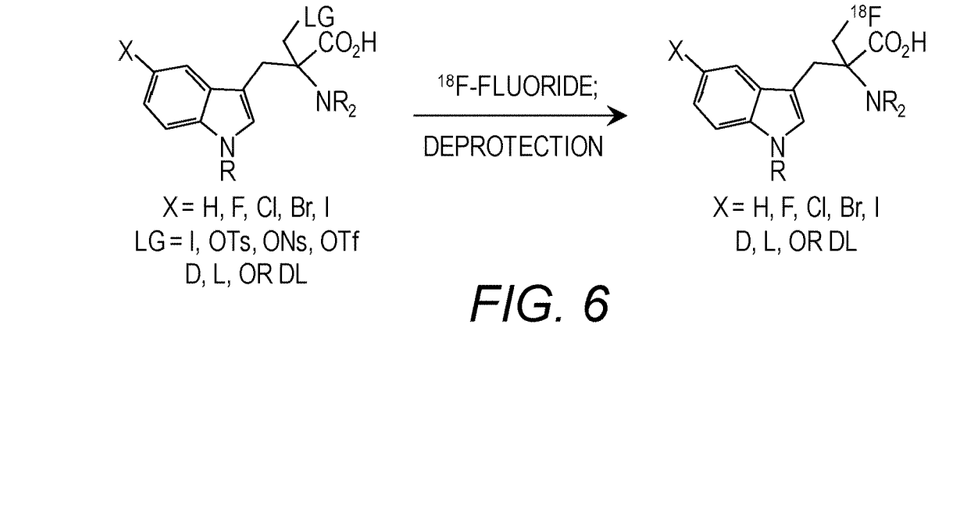
FIG. 6 shows alpha-fluoromethyl tryptophan derivatives for imaging.

Because the structure of the tier 1 compound is very similar to AMT (the atom size of F is similar to H), it is expected to have similar affinity for IDO in vitro. Positions other than the 5 position may be labeled, as shown in FIG. 2. $^{18}$F may also be incorporated in the side chains of AMT (FIG. 4) and other compounds based on the IDO inhibitor 1-Methyl-D-tryptophan or brasinin may be prepared (FIG. 4) These compounds do not require methylation at the amino acid carbon as D-tryptophan cannot participate in protein synthesis.

Examples of compounds and protecting group intermediates of the invention are shown below and in FIGS. 2-6:

1

5F-Trp. D or L

2

6F-Trp. D + L

3

4

5

-continued

6

5F-αMe-Trp L or D

7

6F-αMe-Trp L or D
Similarly, F at other position

8

D amino acid

Similarly, F at other position

9

Similarly, F at other position

10

F-Seratonin

11

12 wherein X is, e.g., alkyl, alkoxy, F, Cl, Br, I, $NO_2$, $NH_2$, OH, $CF_3$, etc. Additional compounds include the compounds above with multiple substituents on the aromatic ring, e.g., F and/or X at other positions.

Thus, one aspect of the invention relates to a $^{18}F$-labeled compound suitable for use as an IDO pathway probe. In some embodiments, the compound is tryptophan or an analog thereof. In some embodiments, the compound is alpha-methyl-tryptophan or an analog thereof. In some embodiments, the compound is 1-methyl-tryptophan or an analog thereof. In some embodiments, the compound is L-tryptophan or an analog thereof. In some embodiments, the compound is D-tryptophan or an analog thereof. In some embodiments, the compound is brasinin or an analog thereof. As used herein, the term "analog" refers to a modified compound (e.g., through the addition or deletion of one or more atoms, e.g., no more than about 5, 10, 15, or 20 atoms) that still functions as a PET probe.

In some embodiments, the compound comprises $^{18}F$ directly or indirectly linked to the aromatic ring at one or more of positions 2, 4, 5, 6, or 7, e.g., at position 5. The numbering of the compounds is as shown in FIG. 1.

In certain embodiments, the $^{18}$F is part of a side chain attached to the aromatic ring, which may be attached at one or more of positions 2, 4, 5, 6, or 7. In one embodiment, the compound comprises at least one group linked to the aromatic ring;
wherein each X is independently C, O, N, or S;
n and m are independently 0-5; and
w is 0 or 1.

In one embodiment, the compound comprises at least one group; wherein n is 0-5.

In certain embodiments, the compound comprises 1, 2, 3, 4, or 5 side chains which may be the same or different.

In certain embodiments, the compound comprises a side chain, e.g., one of the groups described above, at position 1, i.e., linked to the nitrogen. This side chain may be in addition to other side chains linked at other positions of the aromatic ring.

In some embodiment, when the $^{18}$F is part of a side chain attached to the aromatic ring, the compound may comprise one of more additional F linked to the aromatic ring, e.g., directly linked. The additional F may or may not be $^{18}$F.

In certain embodiments, the compounds of the invention exclude compounds that comprise $^{18}$F directly linked to the aromatic ring.

In addition to an $^{18}$F label, the compounds of the invention may further comprise an additional substituent on the aromatic ring. The additional substituent may be a halogen, e.g., F. The additional substituent may be an isotope.

In certain embodiments, the compound of the invention comprises an $^{18}$F label or a non-radioactive F, and further comprises one or more additional isotope atoms. In some embodiments, the additional isotope atom is $^{11}$C. In some embodiments, the additional isotope atom is a radioactive halogen, e.g., $^{123}$I, $^{124}$I, $^{125}$I, $^{131}$I, $^{76}$Br, and/or $^{34m}$Cl. In some embodiments, the additional isotope atom $^{211}$At.

Another aspect of the invention relates to a radioactive compound comprising a therapeutic isotope suitable for use as a therapeutic agent. In some embodiments, the compound is tryptophan or an analog thereof. In some embodiments, the compound is alpha-methyl-tryptophan or an analog thereof. In some embodiments, the compound is 1-methyl-tryptophan or an analog thereof. In some embodiments, the compound is L-tryptophan or an analog thereof. In some embodiments, the compound is D-tryptophan or an analog thereof. In some embodiments, the compound is brasinin or an analog thereof. In some embodiments, the compound is serotonin or melatonin or an analog thereof. As used herein, the term "analog" refers to a modified compound (e.g., through the addition or deletion of one or more atoms, e.g., no more than about 5, 10, 15, or 20 atoms) that still functions as a therapeutic agent.

In some embodiments, the compound comprises a radioactive isotope directly or indirectly linked to the aromatic ring at one or more of positions 2, 4, 5, 6, or 7, e.g., at position 5. The numbering of the compounds is as shown in FIG. 1.

In certain embodiments, the radioactive isotope is part of a side chain attached to the aromatic ring, which may be attached at one or more of positions 2, 4, 5, 6, or 7.

In certain embodiments, the compound comprises 1, 2, 3, 4, or 5 side chains which may be the same or different.

In certain embodiments, the compound comprises a side chain, e.g., one of the groups described above, at position 1, i.e., linked to the nitrogen. This side chain may be in addition to other side chains linked at other positions of the aromatic ring.

In certain embodiments, the radioactive isotope is any isotope that can exert a therapeutic effect, e.g., emits a wave or particle capable of damaging or killing a nearby cell. Examples include, without limitation, $^{123}$I, $^{124}$I, $^{125}$I, $^{131}$I, and $^{211}$At.

In certain embodiments, the compound of the invention is selective for the kynurenine pathway relative to the serotonin pathway. The compound may be metabolized entirely by the kynurenine pathway or may be partially metabolized by the kynurenine pathway such that at least 50% (e.g., at least 60%, 70%, 80%, or 90%) of the compound is metabolized by the kynurenine pathway relative to the serotonin pathway.

Another aspect of the invention relates to a PET probe comprising the compound of the invention.

A further aspect of the invention relates to a composition comprising the compound or probe of the invention and a pharmaceutically acceptable carrier.

An additional aspect of the invention relates to other molecules that may be labeled with $^{18}$F or a therapeutic isotope, e.g., molecules that have an aromatic ring and can be labeled by the methods of the invention. Examples include, without limitation, $^{18}$F-labeled serotonin, $^{18}$F-labeled melatonin, and $^{18}$F-labeled brasinin.

Additional aspects of the invention relate to methods of using the compounds of the invention for imaging or therapy.

One aspect of the invention relates to a method of carrying out a PET scan on a subject, comprising administering to the subject the compound, probe, or composition of the invention. Techniques for carrying out PET scans are well known in the art.

Another aspect of the invention relates to a method of imaging the IDO pathway in a subject, comprising administering to the subject the compound, probe, or composition of the invention.

An additional aspect of the invention relates to a method of predicting the responsiveness of a subject with a solid tumor to a PD-1/PD-L1 inhibitor, comprising carrying out a PET scan on the subject using the compound, probe, or composition of the invention. If the PET scan shows that the compound or probe is present in the tumor, the presence of IDO in the tumor is indicated, which predicts that the tumor will be responsive to a PD-1/PD-L1 inhibitor.

A further aspect of the invention relates to a method of treating a solid tumor in a subject in need thereof, comprising predicting the responsiveness of a subject with a solid tumor to a PD-1/PD-L1 inhibitor by carrying out a PET scan on the subject using the compound, probe, or composition of the invention, and treating the solid tumor based on the results of the PET scan. If the tumor is positive for the compound or probe, the treatment may involve administration of a PD-1/PD-L1 inhibitor. If the tumor is negative for the compound or probe or does not exhibit elevated levels of the compound or probe, an alternative treatment may be administered.

Another aspect of the invention relates to a method of determining whether a solid tumor in a subject contains tumor-infiltrating immune cells, comprising carrying out a PET scan on the subject using the compound, probe, or composition of the invention.

An additional aspect of the invention relates to a method of treating a disease or disorder, e.g., disease involving the IDO pathway, e.g., cancer, e.g., a solid tumor, in a subject in need thereof, comprising administering a therapeutically effective amount of a therapeutic compound of the invention. A "disease involving the IDO pathway" is any disease or condition in which the IDO pathway is relevant to a characteristic of the disease or condition or a symptom of the disease or condition, e.g., a cause or indicator of the characteristic.

In some embodiments, the solid tumor is any tumor type that may involve the IDO pathway. Examples include, without limitation, metastatic melanoma, non-small cell lung cancer, urothelial cancer, renal cell carcinoma, Merkel cell carcinoma, breast cancer, primary brain cancer, prostate cancer, or head and neck cancer.

The present invention is explained in greater detail in the following non-limiting Examples.

Example 1

Activity of Compounds

Figure 7:
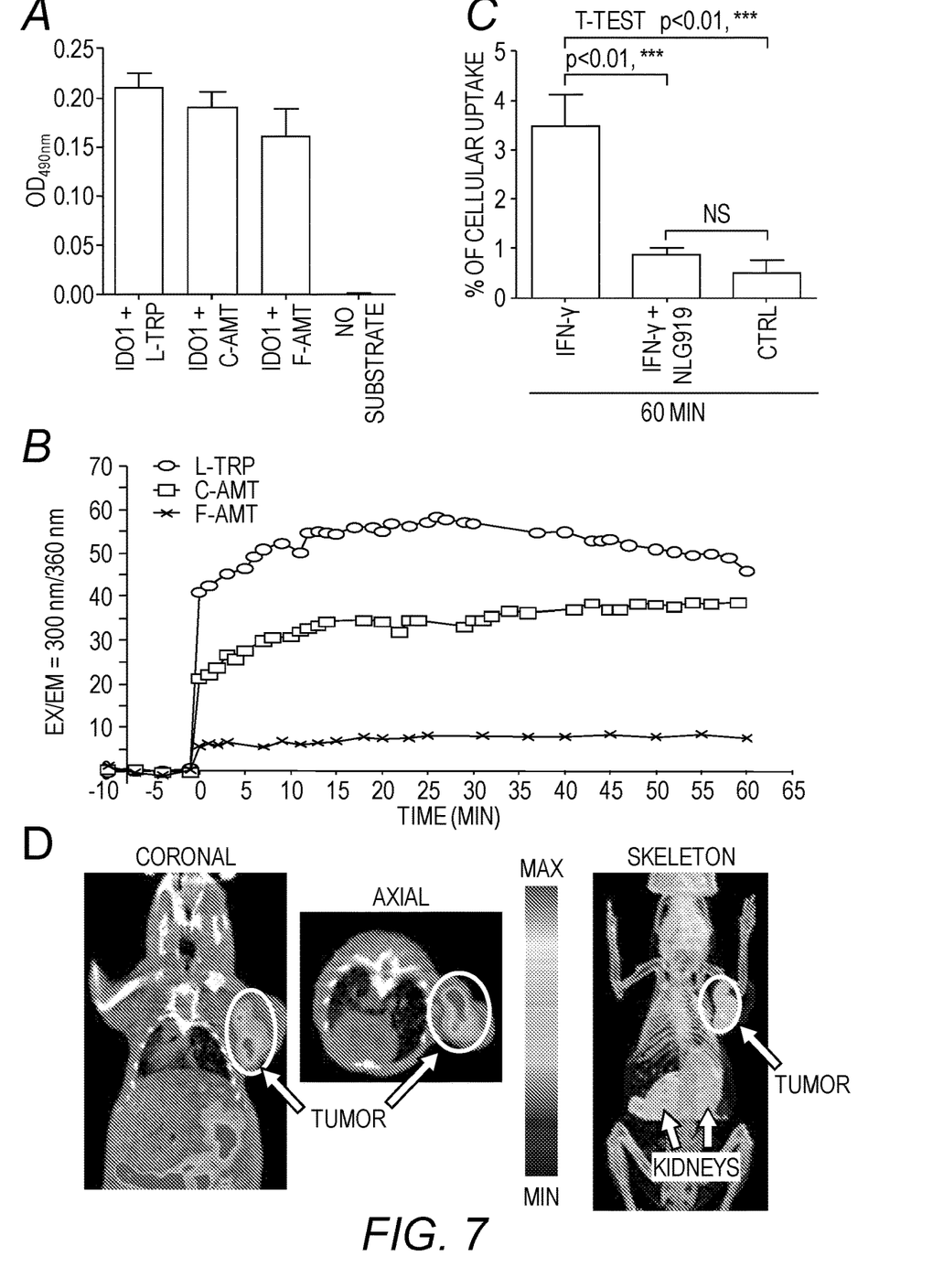
FIGS. 7A-7D show (A) IDO1 enzyme assay demonstrated that L-Trp, C-AMT and 5-F-AMT are substrates to IDO1 enzyme. (B) Protein based assay clearly demonstrated that 5-F-AMT is not a good substrate for Tph (compared with Trp and C-AMT). (C) The HeLa cells uptake of 5-[$^{18}$F]F-AMT increased 7 times after IFN-γ treatment, which could also be successfully reduced by IDO inhibitor NLG919. (D) Decay-corrected whole-body small PET images of B16F10 melanoma after 30 min injection of 5-[$^{18}$F]F-AMT.

Among the agents synthesized, 5-[$^{18}$F]F-AMT was first evaluated in vitro. In order to ensure that 5-[$^{18}$F]F-AMT could be used for IDO imaging, cell- and enzyme-based assays were performed. It was first tested whether 5-[$^{18}$F] F-AMT is a substrate for the IDO enzyme, and the result compared with that of the natural substrate Trp and a known IDO agent, α-methyl-L-tryptophan (AMT). As shown in FIG. 7A, the absorbance at 490 nm for the reaction containing L-Trp, AMT, or F-AMT was 0.21±0.01, 0.19±0.02, and 0.16±0.03 (results from 3 independent assays), while the control reaction system had no absorbance. These results suggested that all three compounds are substrates for IDOL It is known that IFNγ treatment can upregulate IDO1 expression. Therefore, a cell-based assay was performed to further evaluate the agents. The uptake of 5-[$^{18}$F]F-AMT in IFNγ-treated cells was 3.474±0.6451% compared with 0.50±0.28% in control cells after 1 h incubation (p<0.001) (FIG. 7C). When the IFNγ-treated cells were incubated with NLG919, an IDO1 inhibitor, the uptake of 5-[$^{18}$F]F-AMT decreased to 0.88±0.12%, which was comparable with control cells (p>0.05) but significantly lower than that in IFNγ-treated cells) (FIG. 7C). These results indicated that the cell uptake of 5-[$^{18}$F]F-AMT is associated with IDO1 expression levels. The serotonin pathway is a competitive metabolic route for Trp and its derivatives. In the first step Tph adds a hydroxyl group to position 5 of the indole ring. It was evaluated whether the introduction of fluorine at the 5-position would affect metabolism by Tph. As shown in) (FIG. 7B), immediately after adding L-Trp to the reaction system containing the tryptophan hydroxylase enzyme, the fluorescence signal increased from a baseline value of −0.266 to 40.885 and reached a peak value 58.350 at 26 min. Immediately after adding AMT to the reaction system, the fluorescence signal increased from a baseline value of −0.312 to 21.145 and reached a peak value of 36.607 at 34 min. However, adding 5-F-AMT to the reaction system only resulted in an increase to 5.635 (from −1.026), and the peak value was only 8.176 (at 25 min). These results demonstrate that, compared with Trp and AMT, 5-[$^{18}$F]F-AMT is a worse substrate for Tph. This evaluation has demonstrated the great potential of the agents that have been generated.

A tumor xenograft mouse model was produced with a B16F10 melanoma. 200 µCi of 5-$^{18}$F-AMT was injected and a PET image was obtained at 30 min. (FIG. 7D). The image clearly shows the tumor.

Figure 8A:
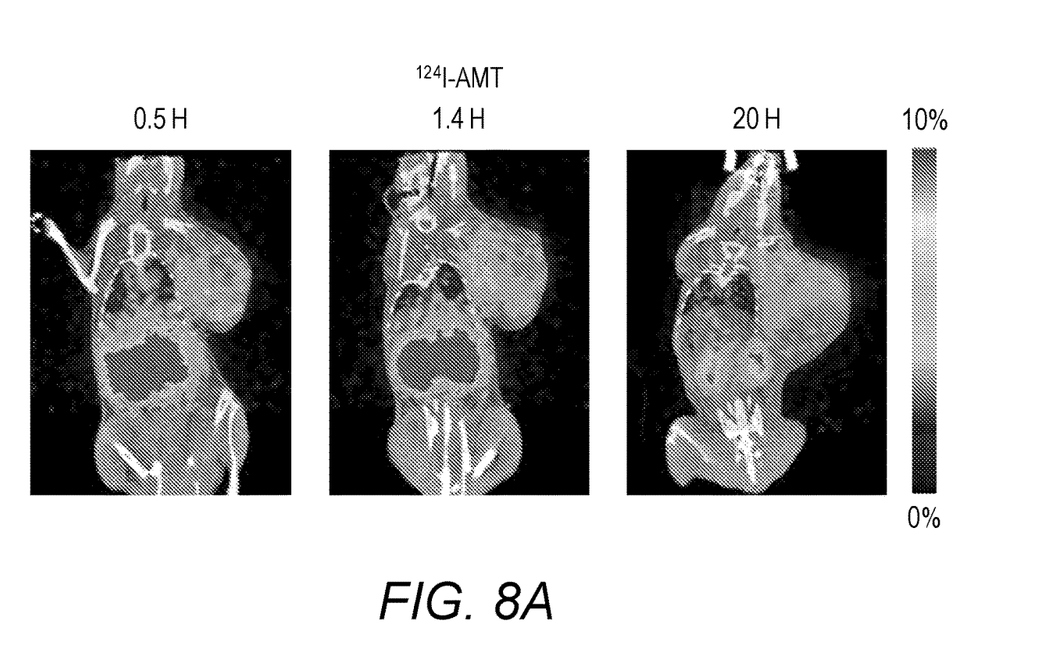
FIGS. 8A-8B show (A) decay-corrected whole-body small PET images of B16F10 melanoma 0.5 h, 1.4 h, and 20 h after injection of $^{124}$I-AMT; (B) decay-corrected whole-body small PET images of B16F10 melanoma 50 min after injection of $^{18}$F—N-Me-Trp.
Figure 8B:
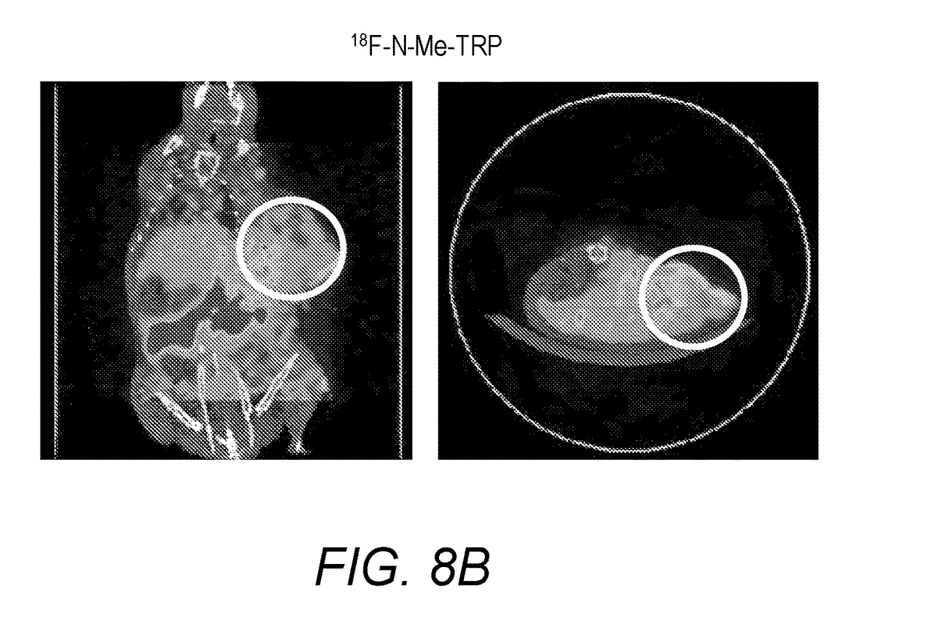

To test the effectiveness of therapeutic compounds of the invention, a tumor $^{124}$I-AMT xenograft mouse model was produced with a B16F10 melanoma. 1 (FIG. 8A) or $^{18}$F—N-Me-Trp (FIG. 8B) were injected in the tail vein and PET images obtained. The results show the accumulation of the compound in the tumor.

The foregoing is illustrative of the present invention, and is not to be construed as limiting thereof. The invention is defined by the following claims, with equivalents of the claims to be included therein. All publications, patent applications, patents, patent publications, and any other references cited herein are incorporated by reference in their entireties for the teachings relevant to the sentence and/or paragraph in which the reference is presented.

What is claimed is:

1. A $^{18}$F-labeled compound suitable for use as an indoleamine-2,3-dioxygenase (IDO) pathway probe, wherein the compound is 5-[$^{18}$F]fluoro-α-methyltryptophan.

2. A positron emission tomography (PET) probe comprising the compound of claim 1.

3. A composition comprising the compound of claim 1 and a pharmaceutically acceptable carrier.

4. A method of carrying out a PET scan on a subject, comprising administering to the subject the compound of claim 1 and performing a PET scan on the subject.

5. A method of imaging the IDO pathway in a subject, comprising administering to the subject the compound of claim 1 and imaging the IDO pathway in the subject.

6. A method of predicting the responsiveness of a subject with a solid tumor to a PD-1/PD-L1 inhibitor, comprising administering to the subject the compound of claim 1, carrying out a PET scan on the subject, and predicting the responsiveness of the subject based on the results of the PET scan.

7. A method of treating a solid tumor in a subject, comprising predicting the responsiveness of a subject with a solid tumor to a PD-1/PD-L1 inhibitor by administering to the subject the compound of claim 1, carrying out a PET scan on the subject, and treating the solid tumor based on the results of the PET scan.

8. A method of determining whether a solid tumor in a subject contains tumor-infiltrating immune cells, comprising administering to the subject the compound of claim 1, carrying out a PET scan on the subject, and determining whether a solid tumor in the subject contains tumor-infiltrating immune cells based on the results of the PET scan.

* * * * *

UNITED STATES PATENT AND TRADEMARK OFFICE
CERTIFICATE OF CORRECTION

PATENT NO. : 11,103,603 B2
APPLICATION NO. : 16/343267
DATED : August 31, 2021
INVENTOR(S) : Li et al.

It is certified that error appears in the above-identified patent and that said Letters Patent is hereby corrected as shown below:

On the Title Page

Item (56) References Cited, FOREIGN PATENT DOCUMENTS, Column 2, Line 3: Please correct "20517922" to read -- 201517922 --

Item (56) References Cited, OTHER PUBLICATIONS, Column 2, Line 11: Please correct "Ferried" to read -- Ferrieri --

Item (56) References Cited, OTHER PUBLICATIONS, Column 2, Line 21: Please correct "Chotellis" to read -- Chiotellis --

In the Specification

Column 6, Line 3: Please correct "5-[$^{18}$]F-AMT" to read -- 5-[$^{18}$F]F-AMT --

Column 7, Line 60: Please correct "*Int* 0.2014" to read -- *Int* .2014 --

Column 11, Line 23: Please correct "Co$_2$Me" to read -- CO$_2$Me --

Column 15, Line 43: Please correct "IDOL" to read -- IDO1 --

Column 16, Lines 16-17: Please correct "tumor $^{124}$I-AMT xenograft mouse model was produced with a B16F10 melanoma. 1 (FIG. 8A)" to read -- tumor xenograft mouse model was produced with a B16F10 melanoma. $^{124}$I-AMT (FIG. 8A) --

Signed and Sealed this
Twenty-fifth Day of January, 2022

Drew Hirshfeld
*Performing the Functions and Duties of the
Under Secretary of Commerce for Intellectual Property and
Director of the United States Patent and Trademark Office*